(12) United States Patent
Kakinuki

(10) Patent No.: US 10,660,829 B2
(45) Date of Patent: May 26, 2020

(54) HYDROGEL COMPOSITION

(71) Applicant: KAO CORPORATION, Tokyo (JP)

(72) Inventor: Kenichi Kakinuki, Edogawa-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/539,728

(22) PCT Filed: Dec. 24, 2015

(86) PCT No.: PCT/JP2015/086099
§ 371 (c)(1),
(2) Date: Jun. 26, 2017

(87) PCT Pub. No.: WO2016/104644

PCT Pub. Date: Jun. 30, 2016

(65) Prior Publication Data

US 2018/0000698 A1  Jan. 4, 2018

(30) Foreign Application Priority Data

Dec. 26, 2014  (JP) .................. 2014-266104

(51) Int. Cl.
| | | |
|---|---|---|
| *A61K 9/00* | (2006.01) | |
| *A61K 8/04* | (2006.01) | |
| *A61Q 19/00* | (2006.01) | |
| *A61K 8/73* | (2006.01) | |
| *A61K 8/81* | (2006.01) | |
| *A61F 7/02* | (2006.01) | |

(52) U.S. Cl.
CPC .............. *A61K 8/042* (2013.01); *A61F 7/02* (2013.01); *A61K 8/731* (2013.01); *A61K 8/8129* (2013.01); *A61K 8/8158* (2013.01); *A61K 8/8176* (2013.01); *A61Q 19/00* (2013.01); *A61F 2007/0214* (2013.01); *A61F 2007/0219* (2013.01); *A61F 2007/0226* (2013.01); *A61K 2800/5422* (2013.01); *A61K 2800/5424* (2013.01)

(58) Field of Classification Search
CPC ..................................................... A61K 8/042
See application file for complete search history.

(56) References Cited

U.S. PATENT DOCUMENTS

| | | |
|---|---|---|
| 2006/0198802 A1 | 9/2006 | Ito et al. |
| 2010/0217170 A1 | 8/2010 | Tsuru et al. |
| 2014/0171555 A1 | 6/2014 | Tani et al. |

FOREIGN PATENT DOCUMENTS

| | | |
|---|---|---|
| CN | 1730595 A | 2/2006 |
| CN | 102144989 A | 8/2011 |
| CN | 102619139 B | 2/2014 |
| JP | 55-17347 A | 2/1980 |
| JP | 10-265373 A | 10/1998 |
| JP | 11-139964 A | 5/1999 |
| JP | 2002-234819 A | 8/2002 |
| JP | 2003-93434 A | 4/2003 |
| JP | 2003-192581 A | 7/2003 |
| JP | 2005-225837 A1 | 8/2005 |
| JP | 2007-126397 A | 5/2007 |
| JP | 2008-238556 A | 10/2008 |
| JP | 2012-188429 A | 10/2012 |
| JP | 2014-31323 A | 2/2014 |
| JP | 2015-123083 A | 7/2015 |
| JP | 2015-124146 A | 7/2015 |
| JP | 2017-25020 A | 2/2017 |
| RU | 2 083 620 C1 | 7/1997 |
| WO | 2004/078165 A1 | 9/2004 |
| WO | 2007-034736 A1 | 3/2007 |
| WO | 2010/114121 A1 | 10/2010 |
| WO | 2013/012000 A1 | 1/2013 |

OTHER PUBLICATIONS

Extended European Search Report dated Jul. 3, 2018 in European Patent Application No. 15873212.3, 8 pages.
International Search Report dated Mar. 1, 2016, in PCT/JP2015/086099, filed Dec. 24, 2015.

*Primary Examiner* — Paul W Dickinson
(74) *Attorney, Agent, or Firm* — Oblon, McClelland, Maier & Neustadt, L.L.P.

(57) ABSTRACT

The present invention relates to a hydrogel composition having excellent gel stability while exerting excellent feeling of use. That is, the present invention relates to a hydrogel composition comprising components (A) to (D) below: (A) water in an amount of 50 mass % or more and 90 mass % or less; (B) an anionic water-soluble polymer compound comprising 80 mass % or more of carboxymethylcellulose or a salt thereof; (C) a crosslinking agent that forms ionic crosslinking with an anionic functional group; and (D) a nonionic water-soluble polymer compound, in an amount of 2.5 mass % or more and 8 mass % or less, represented by formula (1) below:

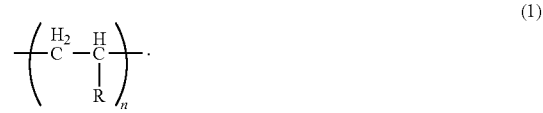

(1)

18 Claims, No Drawings

HYDROGEL COMPOSITION

CROSS REFERENCE TO RELATED APPLICATION

This application is a national stage entry under 35 USC 371 of PCT/JP2015/086099, filed on Dec. 24, 2015, and claims priority to Japanese Patent Application No. 2014-266104 filed on Dec. 26, 2014.

FIELD OF THE INVENTION

The present invention relates to a hydrogel composition.

BACKGROUND OF THE INVENTION

Conventionally, adhesive patches and cataplasms produced using various polymer compounds have been developed, and they give respective desired effects. For example, Patent Literature 1 discloses an adhesive patch for external use composed of an adhesive base layer containing polyvinyl alcohol and polyoxyethylene derivatives, a stretchable support, and a release liner, in which the initial adhesion to the skin and the releasability from the adhesive base layer are enhanced. Further, Patent Literature 2 discloses a cataplasm formed by spreading an adhesive composition having a specific gel strength and a specific elasticity onto a support, the composition containing an aqueous adhesive base containing a water-soluble polymer material and a compound composed of a metal crosslinking agent and an amino acid, with which an appropriate adhesion to the skin is expressed.

Further, Patent Literature 3 discloses a hydrous cataplasm composition containing a specific mineral and a polyacrylic acid and/or a salt thereof, and having a moisture content of 60 weight % or more, with which an attempt to give adhesion to the skin while reducing bleeding from the back is made.

PATENT LITERATURE (Patent Literature 1) JP-A-2003-093434
(Patent Literature 2) JP-A-10-265373
(Patent Literature 3) JP-A-11-139964

SUMMARY OF THE INVENTION

The present invention relates to a hydrogel composition comprising components (A) to (D) below:
(A) water in an amount of 50 mass % or more and 95 mass % or less;
(B) an anionic water-soluble polymer compound comprising 80 mass % or more of carboxymethylcellulose or a salt thereof;
(C) a crosslinking agent that forms ionic crosslinking with an anionic functional group; and (D) a nonionic water-soluble polymer compound, in an amount of 2.5 mass % or more and 8 mass % or less, represented by formula (1) below:

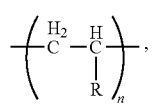

(1)

where R denotes —OH, —NX$_2$ (where X denotes —CH$_3$ or a hydrogen atom), —OCH$_3$, —NHCOCH$_3$, or —NCH$_3$COCH$_3$, and n is a numerical value of from 200 to 500,000.

Further, the present invention relates to a method for producing a hydrogel composition, the method comprising: mixing components (A) to (D) below to prepare an uncrosslinked gel stock solution:
(A) water in an amount of 50 mass % or more and 95 mass % or less;
(B) an anionic water-soluble polymer compound comprising 80 mass % or more of carboxymethylcellulose or a salt thereof;
(C) a crosslinking agent that forms ionic crosslinking with an anionic functional group; and
(D) a nonionic water-soluble polymer compound, in an amount of 2.5 mass % or more and 8 mass % or less, represented by formula (1) below:

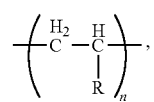

(1)

where R denotes —OH, —NX$_2$ (where X denotes —CH$_3$ or a hydrogen atom), —OCH$_3$, —NHCOCH$_3$, or —NCH$_3$COCH$_3$, and n is a numerical value of from 200 to 500,000; and
subsequently forming the uncrosslinked gel stock solution into a sheet with a peelable film for one surface of the sheet and a peelable film or a base material layer for the other surface.

For the adhesive base as in Patent Literatures 1 and 2, fresh texture tends to be insufficient and stickiness occurs during use. For the composition as in Patent Literature 3, the followability to the skin is insufficient, and the stability of the composition itself can also be improved.

Accordingly, the present invention relates to a hydrogel composition exerting excellent feeling of use and having excellent stability of the gel.

As a result of various studies, the present inventor has found a hydrogel composition, which is capable of effectively enhancing the feeling of use and improving the stability of a gel formed therefrom by containing a specific anionic water-soluble compound and a specific crosslinking agent in combination with a specific amount of a specific nonionic water-soluble polymer compound while having a high content of water.

The hydrogel composition of the present invention has excellent followability to the skin, while giving fresh texture, without uncomfortable feeling of sticking to the skin and can exert comfortable feeling of use, when it is attached onto the skin during use. Further, the hydrogel composition also can be used suitably as an adhesive patch which is subjected to a long-term use, because a gel formed therefrom has excellent stability.

DETAILED DESCRIPTION OF THE INVENTION

Hereinafter, the present invention will be described in detail.

The hydrogel composition of the present invention comprises water in an amount of 50 mass % or more and 95 mass % or less as component (A). Thus, water is present in a high content, and therefore the fresh texture can be exerted well during use, and appropriate flexibility can be exerted also to thereby give the followability to the skin. From the viewpoint of giving the excellent feeling of use, the content of component (A) in the hydrogel composition of the present invention is 50 mass % or more, preferably 60 mass % or more, more preferably 65 mass % or more, further preferably 70 mass % or more, particularly preferably 75 mass % or more. Further, from the viewpoint of ensuring the gel stability, the content of component (A) in the hydrogel composition of the present invention is 95 mass % or less, preferably 92 mass % or less, more preferably 90 mass % or less, further preferably 85 mass % or less. Further, the content of component (A) in the hydrogel composition of the present invention is 50 mass % or more and 95 mass % or less, preferably from 60 to 92 mass %, more preferably from 65 to 92 mass %, further preferably from 70 to 90 mass %, particularly preferably 75 to 85 mass %.

The hydrogel composition of the present invention comprises an anionic water-soluble polymer compound comprising 80 mass % more of carboxymethylcellulose or a salt thereof as component (B). Use of such an anionic water-soluble polymer compound makes it possible to form ionic crosslinking between a carboxyl group contained in the carboxymethylcellulose or a salt thereof and a crosslinking agent of component (C), which will be described below, to thereby form a gel having high water retention and good gel strength. The "water-soluble polymer compound" in the present invention means a compound which is uniformly dissolved in water and gives a viscosity when dispersed in water.

Examples of the salt of carboxymethylcellulose include one or more selected from the group consisting of an ammonium salt and an alkali metal salt such as sodium salt and potassium salt, among which sodium carboxymethyl cellulose is preferable, from the viewpoint of favorably forming the ionic crosslinking and from the viewpoint of the cost and ease of availability or the like. Further, the etherification degree of the carboxymethylcellulose or a salt thereof is preferably from 0.6 to 1.1, more preferably from 0.65 to 0.9, from the viewpoint of maintaining the appropriate gel strength so as to enhance the followability to the skin and ensure the gel stability.

The etherification degree is a degree of substitution of the carboxy methyl group per glucose unit. The etherification degree can be obtained, for example, according to the CMC industrial association analysis method (ashing method). The etherification degree can be determined by accurately weighing 1 g of sodium carboxymethyl cellulose, ashing it at 600° C. in a porcelain crucible, titrating sodium oxide produced by the ashing with N/10 sulfuric acid using phenolphthalein as an indicator, and applying the titer Y mL per gram of sodium carboxymethyl cellulose to the following formula for calculation.

Etherification degree=(162×Y)/(10,000−80×Y)

The viscosity of the carboxymethylcellulose or the salt thereof as a 1 mass aqueous solution at 25° C., as measured using a B-type viscometer, is preferably from 1,500 to 10,000 mPa·s, more preferably from 2,500 to 7,000 mPa·s, from the viewpoint of maintaining the appropriate gel strength so as to enhance the followability to the skin and from the viewpoint of ensuring the gel stability.

The content of the carboxymethylcellulose or a salt thereof in the anionic water-soluble polymer compound of component (B) is 80 mass % or more, preferably 90 mass % or more, more preferably 95 mass % or more, and is preferably 100 mass % or less, from the viewpoint of having both of good feeling of use and high gel stability. Examples of methods for analyzing the content of the carboxymethylcellulose or a salt thereof include nuclear magnetic resonance (NMR) method, liquid chromatography mass spectrometry (LC/MS), and gas chromatograph mass spectrometry (GC/MS).

Anionic water-soluble polymer compounds which may be contained in the anionic water-soluble polymer compound of component (B) other than the aforementioned carboxymethylcellulose or a salt thereof are compounds in which only anionic functional groups are present as polar groups in a molecule, and specific examples of such compounds include poly(meth)acrylic acid or a salt thereof, polystyrene sulfonic acid or a salt thereof, polyisoprene sulfonic acid or a salt thereof, polyvinyl naphthalene sulfonic acid or a salt thereof, polyvinyl sulfonic acid or a salt thereof, poly(meth)acrylamido-dimethylpropanesulfonic acid or a salt thereof, poly(meth)acryloyloxyethylsulfonic acid or a salt thereof, and anionic starch derivatives.

The content of component (B) in the hydrogel composition of the present invention is preferably 2.2 mass % or more, more preferably 2.7 mass % or more, further preferably 3 mass % or more, from the viewpoint of favorably forming the ionic crosslinking between the carboxyl group contained in the carboxymethylcellulose or a salt thereof and the crosslinking agent of component (C), which will be described below. Further, the content of component (B) in the hydrogel composition of the present invention is preferably 6 mass % or less, more preferably 5 mass % or less, further preferably 4 mass % or less, from the viewpoint of giving the gel appropriate flexibility and the followability to the skin. Further, the content of component (B) in the hydrogel composition of the present invention is preferably from 2.2 to 6 mass %, more preferably from 2.7 to 5 mass %, further preferably from 3 to 4 mass %.

The hydrogel composition of the present invention comprises a crosslinking agent that forms ionic crosslinking with an anionic functional group, as component (C). The crosslinking agent can form the ionic crosslinking with the carboxyl group of the aforementioned carboxymethylcellulose or a salt thereof contained in component (B), to thereby form a gel having high water retention and good gel strength. The crosslinking agent of component (C) needs only to be a cationic compound which can form ionic crosslinking with an anionic functional group, and specific examples thereof include one or more selected from the group consisting of a polyvalent metal compound and a compound having at least two monovalent cation elements and/or amino groups in one molecule. Among these, the polyvalent metal compound is preferable, from the viewpoint of the gel strength and the gel stability. Further, the upper limit of the number of monovalent cation elements and/or amino groups contained in one molecule is preferably 8 or less since a low-molecular compound is preferable as the crosslinking agent.

Examples of the polyvalent metal compound include a compound containing a polyvalent metal such as aluminum, magnesium, titanium, chromium, manganese, iron, cobalt, nickel, zinc, cadmium, lead, and calcium, or a salt of these. Specifically, examples thereof include a polyvalent metal hydroxide such as aluminum hydroxide, calcium hydroxide, magnesium hydroxide, zinc hydroxide, and magnesium aluminum hydroxide; a polyvalent metal oxide such as aluminum oxide, calcium oxide, magnesium oxide, zinc oxide, and sodium aluminate; a polyvalent metal inorganic salt such as aluminum sulfate, potassium aluminum sulfate, ammonium aluminum sulfate, aluminum carbonate, aluminum nitrate, aluminum chloride, calcium sulphate, calcium carbonate, calcium chloride, magnesium sulfate, magnesium carbonate, magnesium chloride, zinc sulfate, zinc carbonate, zinc chloride, magnesium alumino(meta)silicate, and synthetic hydrotalcite; and polyvalent metal organic salts of alkaline earth metal salts such as aluminum acetate, calcium acetate, magnesium acetate, zinc acetate, aluminum lactate, aluminum stearate, aluminum myristate, aluminum glycinate, aluminum benzoate, allantoin chlorohydroxyaluminum, and calcium or magnesium of thioglycolic acid. Among these, from the viewpoint of easily controlling reaction speed in crosslinking, one or more selected from the group consisting of the polyvalent metal hydroxide and the polyvalent metal inorganic salt are preferable, and aluminum hydroxide or magnesium alumino(meta)silicate is more preferable.

Examples of the compound containing a plurality of monovalent cation elements or amino groups in one molecule include a compound having a comparatively low molecular weight such as ethylene hexamethyl diamine dichloride and ethylenediamine, and a cationic polymer compound.

Examples of the cationic polymer compound include polyvinyl pyridine, cationized hydroxyethyl cellulose, poly(meth)acryloyloxyethyl tri(di,mono)alkylammonium chloride, poly(meth)acrylamide ethyl tri(di,mono)alkylammonium chloride, polyethyleneimine polyamine, and a cationic amino acid polymer such as polylysine.

The content of component (C) in the hydrogel composition of the present invention is preferably 0.01 mass % or more, more preferably 0.05 mass % or more, further preferably 0.1 mass % or more, from the viewpoint of favorably forming the ionic crosslinking with component (B). Further, the content of component (C) in the hydrogel composition of the present invention is preferably 2 mass % or less, more preferably 1 mass % or less, further preferably 0.4 mass % or less, from the viewpoint of giving the gel the appropriate flexibility and the followability to the skin. Further, the content of component (C) in the hydrogel composition of the present invention is preferably from 0.01 to 2 mass %, more preferably from 0.05 to 1 mass %, further preferably from 0.1 to 0.4 mass %.

The mass ratio of component (B) to component (C), ((B)/(C)), is preferably 3 or more, more preferably 15 or more, further preferably 20 or more, from the viewpoint of efficiently forming the ionic crosslinking and maintaining the appropriate gel strength. Further, the mass ratio of component (B) to component (C), ((B)/(C)), is preferably 60 or less, more preferably 40 or less, further preferably 30 or less, from the viewpoint of maintaining the flexibility of the gel and ensuring good followability to the skin. Further, the mass ratio of component (B) to component (C), ((B)/(C)), is preferably from 3 to 60, more preferably from 15 to 40, further preferably from 20 to 30.

The hydrogel composition of the present invention comprises a nonionic water-soluble polymer compound, in an amount of 2.5 mass % or more and 8 mass % or less, represented by formula (1) below, as component (D):

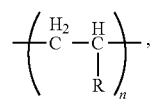
(1)

where R denotes —OH, —NX$_2$ (where X denotes —CH$_3$ or a hydrogen atom), —OCH$_3$, —NHCOCH$_3$, or —NCH$_3$COCH$_3$, and n is a numerical value of 200 to 500,000.

By containing such a nonionic water-soluble vinyl polymer compound in the specific amount described above, the stability of the gel formed from component (B) and component (C) can be effectively ensured while the excellent feeling of use is exerted. Examples of the nonionic water-soluble polymer compound of component (D) include one or more selected from the group consisting of polyvinyl alcohol (PVA), polyvinylmethylether (PVME), polyvinylpyrrolidone (PVP), polyacrylamide, and polyvinylpyrrolidone-vinyl acetate copolymer. Among these, one or more selected from the group consisting of polyvinyl alcohol, polyvinylpyrrolidone, and polyacrylamide are preferable, and polyvinyl alcohol is more preferable, from the viewpoint of effectively ensuring the gel stability.

The content of component (D) in the hydrogel composition of the present invention is 2.5 mass % or more, preferably 3 mass % or more, more preferably 4 mass % or more, from the viewpoint of favorably ensuring the gel stability. Further, the content of component (D) in the hydrogel composition of the present invention is 8 mass % or less, preferably 7 mass % or less, more preferably 6 mass % or less, from the viewpoint of maintaining the flexibility of the gel and ensuring the good followability to the skin. Further, the content of component (D) in the hydrogel composition of the present invention is 2.5 mass % or more and 8 mass % or less, preferably from 3 to 7 mass %, more preferably from 4 to 6 mass %.

The mass ratio of component (B) to component (D) ((B)/(D)) is preferably 0.4 or more, more preferably 0.5 or more, further preferably 0.6 or more, from the viewpoint of providing less residual feeling on the skin for hydrogel composition when an adhesive patch produced using the hydrogel composition of the present invention is attached onto the skin and thereafter is peeled off. Further, the mass ratio of component (B) to component (D), ((B)/(D)), is preferably 1.7 or less, more preferably 1.2 or less, further preferably 0.9 or less, from the viewpoint of the firmly fixing while attached onto the skin. Further, the mass ratio of component (B) to component (D), ((B)/(D)), is preferably from 0.4 to 1.7, more preferably from 0.5 to 1.2, further preferably from 0.6 to 0.9.

The mass ratio of component (A) to components (B) and (D), ((A)/((B)+(D))), is preferably 15 or less, more preferably 12 or less, from the viewpoint of the high gel stability, and the mass ratio is preferably 6 or more, more preferably 7 or more, from the viewpoint of the good feeling of use.

The hydrogel composition of the present invention can contain an organic acid other than the aforementioned components, from the viewpoint of further enhancing the gel stability. Specific examples of such an organic acid include one or more selected from the group consisting of succinic acid, fumaric acid, malic acid, adipic acid, tartaric acid, benzoic acid, citric acid, pyrrolidone carboxylic acid, and salicylic acid. Among these, one or more selected from the group consisting of succinic acid, malic acid, and tartaric acid are preferable, and succinic acid is more preferable, from the viewpoint of possibly contributing to improvement in gel stability.

The content of an organic acid in the hydrogel composition of the present invention is preferably from 0.1 to 0.7 mass %, more preferably from 0.3 to 0.5 mass %, for effectively contributing to the improvement in gel stability.

Inclusion of a water-soluble polymer compound other than component (B) and component (D) in the hydrogel composition of the present invention is preferably limited, from the viewpoint of ensuring the excellent feeling of use and high gel stability while having a high moisture content. Specific examples of the water-soluble polymer compound other than component (B) and component (D) include gelatin, starch (excluding anionic starch derivatives), methyl cellulose, hydroxyethyl cellulose, hydroxypropyl cellulose, hydroxypropyl methyl cellulose, guar gum, and xanthan gum. The content of the water-soluble polymer compound other than component (B) and component (D) is preferably 1 mass % or less, more preferably 0.5 mass % or less, further preferably 0.2 mass % or less. In particular, it is preferable not to contain starch, guar gum, and xanthan gum, except when they are inevitably contained.

The hydrogel composition of the present invention may appropriately contain components which are generally used for cosmetics and pharmaceutical products, such as a humectant, an oil agent, a surfactant, a medicinal component, a preservative, an antioxidant, an ultraviolet absorber, a solubilizer, a colorant, a cooling agent, a warming agent, and a perfume, other than the aforementioned components.

The thickness of the hydrogel composition of the present invention is preferably 0.1 mm or more, more preferably 0.3 mm or more, further preferably 0.5 mm or more, and is preferably 4 mm or less, more preferably 3 mm or less, further preferably 2 mm or less, from the viewpoint of giving the excellent feeling of use such as good texture and ensuring shape retention while exerting appropriate flexibility to give the excellent followability to the skin.

The hydrogel composition of the present invention can be produced according to the following method. For example, the method is a method comprising mixing the aforementioned components (A), (B), (C), and (D), to prepare an uncrosslinked gel stock solution and subsequently forming the uncrosslinked gel stock solution into a sheet with a peelable film for one surface of the sheet and a peelable film or a base material layer for the other surface. Specifically, first, the aforementioned components (A), (B), (C), and (D), and other components, as needed, are mixed to prepare an uncrosslinked gel stock solution. Subsequently, the uncrosslinked gel stock solution is formed into a sheet by sandwiching the uncrosslinked gel stock solution between a peelable film for one surface of the sheet and a peelable film or a base material layer for the other surface and spreading the uncrosslinked gel stock solution using a Baker applicator or the like to have a thickness of from 0.1 to 5 mm, or by applying the uncrosslinked gel stock solution onto a peelable film to have a thickness of from 0.1 to 5 mm and layering a peelable film or a base material layer thereon. Further, the thus obtained sheet is aged for from 1 to 8 days under heating at 30 to 60° C. for progressing crosslinking so that the hydrogel composition of the present invention is obtained. In the present invention, a hydrogel composition which has not undergone the step of progressing crosslinking is referred to as "uncrosslinked gel stock solution".

Further, an adhesive patch can be produced by using the hydrogel composition of the present invention formed into layers as a gel layer and layering a release layer such as a film and a base layer such as non-woven fabric thereon. Examples of the layering method include a method in which one or both of the surfaces sandwiching the aforementioned gel stock solution is a base layer or a release layer, and a method in which a gel layer composed of the hydrogel composition is prepared and thereafter a base layer or a release layer is pressed against the gel layer for layering.

From the viewpoint of the handleability, the hydrogel composition of the present invention is preferably used by being layered on a base material layer such as non-woven fabric, woven fabric, knitted fabric, or paper, and it is more preferably used by being layered on non-woven fabric. When a conventional hydrogel composition is layered on a base material layer, hydrophobic material is generally used for constituting the base material layer from the viewpoint of reducing gel bleed, but the hydrogel composition of the present invention effectively reduces the gel bleed even if a hydrophilic material is used as the base material layer. Therefore, any material can be selected as the base material layer depending on the purpose. For example, in the case of using the hydrogel composition of the present invention as an adhesive sheet for cooling, non-woven fabric containing hydrophilic fibers is preferably used as the base material layer to be layered from the viewpoint of improving the cooling effect.

Examples of materials of the hydrophilic fibers include fibers such as rayon, cotton, cupra, hemp, wool, silk, acetate, cellulose, wood pulp, and non-wood pulp; fibers composed of a polymer having a hydrophilic group such as a hydroxy group, a carboxyl group, a sulfonic acid group, an amide group, and an amino acid group, that is, a hydrophilic polymer such as polyvinyl alcohol, polyethylene glycol, cellulose acetate, polyacrylamide, melamine resin, nylon, and hydrophilic polyurethane; fibers composed of a hydrophilized hydrophobic polymer such as hydrophilized polyester; and composite fibers including a hydrophobic part composed of a hydrophobic polymer such as polyethylene and polypropylene and a hydrophilic part. One of these may be used alone, or two or more of these may be used in combination. Examples of the composite fibers include fibers having a core-sheath structure composed of a core and a sheath. Further, such fiber may have a porous structure which contains voids holding moisture inside the fibers. Among these, a fiber sheet containing one or more hydrophilic fibers selected from the group consisting of rayon, cotton, cupra, cellulose, pulp, and polyvinyl alcohol (PVA), or a mixed fiber sheet containing these hydrophilic fibers and hydrophobic fibers is more preferable. In particular, a fiber sheet containing one or more hydrophilic fibers selected from the group consisting of rayon, cellulose, pulp, and polyvinyl alcohol, or a mixed fiber sheet containing these hydrophilic fibers and hydrophobic fibers is further more preferable.

Examples of materials for the hydrophobic fibers include fibers composed of a hydrophobic polymer such as polyolefins, e.g., polyethylene terephthalate (PET), polyethylene (PE), and polypropylene (PP), and polyurethanes.

In the case of using the hydrogel composition of the present invention as an adhesive sheet for cooling by layering it onto a base material layer, the content of hydrophilic fibers in the non-woven fabric used as the base material layer is preferably over 20 mass %, more preferably 30 mass % or more, further preferably 40 mass % or more, even more preferably 50 mass % or more in the non-woven fabric from the viewpoint of promoting moisture transfer from the hydrogel composition layer to the fibers of the non-woven fabric sheet and promoting moisture evaporation from the fibers very well. Further, the content of the hydrophilic fibers in the non-woven fabric used as the base material layer may be 100 mass %, but is preferably 100 mass % or less, more preferably 95 mass % or less, further preferably 90 mass % or less in the non-woven fabric from the viewpoint of reducing the bleed of the hydrogel composition from the base material layer. In this case, non-woven fabric having a specific composition may be used alone, or a plurality of non-woven fabrics having different compositions may be layered, as the base material layer to be layered on the hydrogel composition. However, the overall content of the hydrophilic fibers in the non-woven fabrics used as the base material layer preferably falls within the aforementioned range.

The hydrogel composition of the present invention is preferably used, for example, by forming the gel layer as described above to produce an adhesive patch and attaching the surface of the gel layer onto the skin. The hydrogel composition of the present invention can exert excellent followability to the skin and comfortable feeling of use without uncomfortable feeling of sticking to the skin, while giving fresh texture, upon application. Further, the stability of a gel formed is also excellent, thereby enabling long-term use while maintaining the comfortable feeling of use. Accordingly, the hydrogel composition of the present invention is used for a wide range of applications such as cosmetics, pharmaceutical products, quasi drugs, and miscellaneous goods, which are attached onto the skin (including the scalp), and can realize comfortable use by being attached onto the skin in a desired portion.

Concerning the aforementioned embodiments, the present invention further discloses the following hydrogel compositions:

[1] A hydrogel composition comprising components (A) to (D) below:

(A) water in an amount of 50 mass % or more and 95 mass % or less;

(B) an anionic water-soluble polymer compound comprising 80 mass % or more of carboxymethylcellulose or a salt thereof;

(C) a crosslinking agent that forms ionic crosslinking with an anionic functional group; and (D) a nonionic water-soluble polymer compound, in an amount of 2.5 mass % or more and 8 mass % or less, represented by formula (1) below:

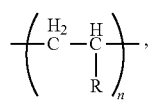

(1)

where R denotes —OH, —NX$_2$ (where X denotes —CH$_3$ or a hydrogen atom), —OCH$_3$, —NHCOCH$_3$, or —NCH$_3$COCH$_3$, and n is a numerical value of from 200 to 500,000;

[2] The hydrogel composition according to [1] above, wherein a content of the component (A) is preferably 60 mass % or more, more preferably 65 mass % or more, further preferably 70 mass % or more, particularly preferably 75 mass % or more, and is preferably 92 mass % or less, more preferably 90 mass % or less, further preferably 85 mass % or less;

[3] The hydrogel composition according to [1] or [2] above, wherein an etherification degree of the carboxymethylcellulose or a salt thereof contained in component (B) is preferably from 0.6 to 1.1, more preferably from 0.65 to 0.9;

[4] The hydrogel composition according to any one of [1] to [3] above, wherein a viscosity at 25° C. of a 1 mass % aqueous solution of the carboxymethylcellulose or a salt thereof contained in the component (B) is preferably from 1,500 to 10,000 mPa·s, more preferably from 2,500 to 7,000 mPa·s;

[5] The hydrogel composition according to any one of [1] to [4] above, wherein a content of the carboxymethylcellulose or a salt thereof in the component (B) is preferably 80 mass % or more, more preferably 90 mass % or more, further preferably 95 mass % or more, and is preferably 100 mass % or less;

[6] The hydrogel composition according to any one of [1] to [5] above, wherein a content of the component (B) is preferably 2.2 mass % or more, more preferably 2.7 mass % or more, further preferably 3 mass % or more, and is preferably 6 mass % or less, more preferably 5 mass % or less, further preferably 4 mass % or less;

[7] The hydrogel composition according to any one of [1] to [6] above, wherein the component (C) is preferably one or more selected from the group consisting of a polyvalent metal compound and a compound having at least two monovalent cation elements and/or amino groups in one molecule, more preferably one or more selected from the group consisting of a polyvalent metal hydroxide, a polyvalent metal oxide, a polyvalent metal inorganic salt, a polyvalent metal organic salt, ethylene hexamethyl diamine dichloride, ethylenediamine, and a cationic polymer compound, further preferably one or more selected from the group consisting of a polyvalent metal hydroxide and a polyvalent metal inorganic salt;

[8] The hydrogel composition according to any one of [1] to [7] above, wherein a content of the component (C) is preferably 0.01 mass % or more, more preferably 0.05 mass % or more, further preferably 0.1 mass % or more, and is preferably 2 mass % or less, more preferably 1 mass % or less, further preferably 0.4 mass % or less;

[9] The hydrogel composition according to any one of [1] to [8] above, wherein a mass ratio of the component (B) to the component (C), ((B)/(C)), is preferably 3 or more, more preferably 15 or more, further preferably 20 or more, and is preferably 60 or less, more preferably 40 or less, further preferably 30 or less;

[10] The hydrogel composition according to any one of [1] to [9] above, wherein the component (D) is preferably one or more selected from the group consisting of polyvinyl alcohol, polyvinylmethylether, polyvinylpyrrolidone, polyacrylamide, and polyvinylpyrrolidone-vinyl acetate copolymer, more preferably one or more selected from the group consisting of polyvinyl alcohol, polyvinylpyrrolidone, and polyacrylamide;

[11] The hydrogel composition according to any one of [1] to [10] above, wherein a content of the component (D) is preferably 3 mass % or more, more preferably 4 mass % or more, and is 8 mass % or less, preferably 7 mass % or less, more preferably 6 mass % or less;

[12] The hydrogel composition according to any one of [1] to [11] above, wherein a mass ratio of the component (B) to the component (D), ((B)/(D)), is preferably 0.4 or more, more preferably 0.5 or more, further preferably 0.6 or more, and is preferably 1.7 or less, more preferably 1.2 or less, further preferably 0.9 or less;

[13] The hydrogel composition according to any one of [1] to [12] above, further comprising an organic acid, wherein the organic acid is preferably one or more selected from the group consisting of succinic acid, fumaric acid, malic acid, adipic acid, tartaric acid, benzoic acid, citric acid, pyrrolidone carboxylic acid, and salicylic acid, more preferably one or more selected from the group consisting of succinic acid, malic acid, and tartaric acid, further preferably succinic acid;

[14] The hydrogel composition according to [13] above, wherein a content of the organic acid is preferably from 0.1 to 0.7 mass %, more preferably from 0.3 to 0.5 mass %;

[15] The hydrogel composition according to any one of [1] to [14] above, wherein a content of water-soluble polymer compounds other than the component (B) and the component (D) is preferably 1 mass % or less, more preferably 0.5 mass % or less, further preferably 0.2 mass % or less, or preferably starch, guar gum, or xanthan gum is not contained;

[16] The hydrogel composition according to any one of [1] to [15] above, wherein the hydrogen composition has a thickness of preferably 0.1 mm or more, more preferably 0.3 mm or more, further preferably 0.5 mm or more, and is preferably 4 mm or less, more preferably 3 mm or less, further preferably 2 or less;

[17] The hydrogel composition according to any one of [1] to [16] above, which is layered preferably on non-woven fabric, woven fabric, knitted fabric, or paper, more preferably on non-woven fabric as a base material layer;

[18] The hydrogel composition according to [17] above, wherein the non-woven fabric preferably contains hydrophilic fibers, more preferably contains one or more selected from the group consisting of fibers of rayon, cotton, cupra, hemp, wool, silk, acetate, cellulose, wood pulp, or non-wood pulp; fibers composed of a hydrophilic polymers including polyvinyl alcohol, polyethylene glycol, cellulose acetate, polyacrylamide, melamine resin, nylon, and hydrophilic polyurethane; fibers composed of a hydrophilized hydrophobic polymer; and composite fibers having a hydrophobic part composed of a hydrophobic polymer and a hydrophilic part;

[19] The hydrogel composition according to [18] above, wherein a content of the hydrophilic fibers in the non-woven fabric is preferably over 20 mass %, more preferably 30 mass % or more, further preferably 40 mass % or more, particularly preferably 50 mass % or more, and is preferably 100 mass % or less, more preferably 95 mass % or less, further preferably 90 mass % or less;

[20] An adhesive sheet for cooling comprising the hydrogel composition according to any one of [1] to [19] above layered on a base material layer;

[21] Use of the hydrogel composition according to any one of [1] to [19] above for producing an adhesive sheet for cooling by layering on a base material layer;

[22] A method for producing a hydrogel composition, comprising: mixing the aforementioned components (A), (B), (C), and (D) to prepare an uncrosslinked gel stock solution, and subsequently forming the uncrosslinked gel stock solution into a sheet with a peelable film for one surface of the sheet and a peelable film or a base material layer for the other surface;

[23] The method for producing a hydrogel composition according to [22] above, wherein the method for forming the uncrosslinked gel stock solution into a sheet is a method comprising sandwiching the uncrosslinked gel stock solution between a peelable film for one surface of the sheet and a peelable film or a base material layer for the other surface and then spreading the uncrosslinked gel stock solution, or a method comprising applying the uncrosslinked gel stock solution onto a peelable film and layering a peelable film or a base layer thereon;

[24] The method for producing a hydrogel composition according to [23] above, wherein the uncrosslinked gel stock solution is spread or applied preferably to a thickness of from 0.1 to 5 mm;

[25] The method for producing a hydrogel composition according to any one of [22] to [24] above, wherein the uncrosslinked gel stock solution is aged preferably for 1 to 8 days under heating at 30 to 60° C.; and

[26] The method for producing a hydrogel composition according to any one of [22] to [25] above, wherein the hydrogel composition is layered preferably on non-woven fabric, woven fabric, knitted fabric, or paper, more preferably on non-woven fabric as a base material layer.

EXAMPLES

Hereinafter, the present invention will be specifically described based on examples. The content of each component is shown as mass %, unless otherwise specified in the tables.

Examples 1 to 23 and Comparative Examples 1 to 6

According to the prescription shown in Tables 1 to 3, an adhesive patch containing a hydrogel composition was produced by the following method.

Specifically, a mixed solution of propylene glycol in which glycerin and methyl paraoxybenzoate were dissolved by heating, sodium carboxymethyl cellulose, and dried aluminum hydroxide gel was first put into a kneader, and then a succinic acid aqueous solution was added thereto, to prepare an uncrosslinked gel stock solution. Subsequently, the obtained uncrosslinked gel stock solution was sandwiched between polyethylene terephthalate (PET) films and was spread using a Baker applicator to adjust the thickness of the gel stock solution to 0.8 mm. Subsequently, one of the PET films was peeled, and non-woven fabric (pulp:PET=80 mass %:20 mass %, basis weight=20 g/m², air-laid, and thickness: 0.22 mm) was layered onto the spread gel layer, to form a sheet-like adhesive patch. The obtained adhesive patch was enclosed in an aluminum pillow package and hermetically sealed therein, followed by aging at 50° C. for 2 days, thereby allowing crosslinking reaction to proceed in the uncrosslinked gel stock solution to form a gel. The adhesive patch including the gel layer after crosslinking was die cut, to obtain a test piece (50 mm×100 mm).

Using the obtained test piece, each evaluation was performed according to the following method.

Tables 1 to 3 show the results.

<<Evaluation of Feeling of Use>>

The feeling of use when the test piece of the adhesive patch thus obtained was attached to the forehead was evaluated by 5 evaluators based on the following criteria, and the average was rounded off to give an evaluation value.

5: Fresh and not sticky at all
4: Fresh and slightly sticky
3: A little sticky
2: Dry but sticky
1: Dry but very sticky <<Evaluation of Adhesion>>

For adhesion, a test was performed according to the method described below with reference to JIS Z 0237 (revised edition in 2009) "Inclined ball tack". The test piece (100 mm×50 mm) of the patch obtained above was attached onto a polyethylene plate inclined at an angle of 30° to the horizontal. A ball made of high carbon chromium bearing steel defined in JIS G 4805 (revised edition in 2008) and having a "nominal" ball size, as defined in JIS B 1501 (revised edition in 2009), of ⅛ inch was put on the top of the test piece and was allowed to roll by gravity, and the time required to pass through the distance of 50 mm between 50 mm point and 100 mm point from the point where the ball had been placed was measured. The time obtained by this measurement serves as an index of the stickiness of the adhesive patch to the skin, and when the time is excessively long, the stickiness is high, which is not preferable from the viewpoint of the texture. The time is preferably less than 200 seconds, more preferably 5 seconds or more and less than 120 seconds, further preferably 10 seconds or more and less than 60 seconds.

<<Evaluation of Sheet Followability>>

The test piece of the patch thus obtained was attached to the skin of the forehead, and the sheet followability when the forehead was moved up and down 1 cm 5 times (1 time/second) was evaluated based on the following criteria. The evaluation was made by 5 evaluators, and the average was rounded off to give an evaluation value.

5: Steadily following without sense of resistance
4: Following with slight sense of resistance
3: Following with sense of resistance
2: Not following and easily peeled with sense of resistance even with slight movement
1: Not following and easily peeled with strong sense of resistance even with slight movement <<Evaluation of Gel Stability>>

The shape retention of the gel after the test piece of the adhesive patch thus obtained was stored at 50° C. for one month was evaluated based on the following criteria. The evaluation was made by 5 evaluators, and the average was rounded off to give an evaluation value.

5: Very high shape retention with elasticity
4: High shape retention with elasticity
3: Slightly low shape retention with elasticity and slight softness
2: Low shape retention with a little elasticity and softness
1: No shape retention of gel without elasticity <<Evaluation of Hydrogel Bleed to Non-Woven Fabrics>>

Test pieces of adhesive patches were produced by layering non-woven fabrics having the following material compositions to each of the test pieces of the adhesive patches obtained in Example 1, and Comparative Examples 4, 5, and 6.

Non-woven fabric 1: Air-laid non-woven fabric (thickness: 0.22 mm and basis weight: 20 $g/m^2$) with PET:pulp=80:20 (mass ratio)

Non-woven fabric 2: Wet double layer non-woven fabric (thickness: 0.13 mm and basis weight: 24 $g/m^2$) with upper layer of rayon:pulp:PP+PET:PVA=37:32:28:3 (mass ratio) and lower layer of PET+PE:pulp:PVA=82:14:4 (mass ratio)

After the produced test piece was stored at 50° C. for one month, the hydrogel bleed to the surface of the non-woven fabric opposite to the surface thereof in contact with the hydrogel was evaluated based on the following criteria.

Table 4 shows the results.

5: Bleed cannot be observed at all on surface of non-woven fabric.
4: Bleed can be observed in ¼ or more of surface of non-woven fabric.
3: Bleed can be observed in half or more of surface of non-woven fabric.
2: Bleed can be observed in ¾ or more of surface of non-woven fabric.
1: Bleed can be observed in entire surface of non-woven fabric.

<<Measurement of Thickness of Hydrogel Layer>>

The thickness of the sheet-like adhesive patch produced in the aforementioned examples was measured at a pressure load of 3.7 $gf/cm^2$, using a constant-pressure thickness gauge PG-11J (manufactured by TECLOCK Corporation) according to JIS K6402:1976. As a result, the thickness of the adhesive patch containing the hydrogel composition according to Examples 1 to 23 and Comparative Examples 1 to 6 was 1.3±0.3 mm. Further, the thickness of the hydrogel layer measured by peeling off only the hydrogel layer from the non-woven fabric layer was 1.1±0.3 mm.

TABLE 1

| | Components blended | Example 1 | Example 2 | Example 3 | Example 4 | Example 5 | Example 6 | Example 7 | Example 8 | Example 9 | Example 10 | Example 11 | Example 12 | Example 13 |
|---|---|---|---|---|---|---|---|---|---|---|---|---|---|---|
| (A) | Purified water | 79.299 | 90.000 | 84.299 | 74.999 | 69.999 | 64.999 | 59.999 | 54.999 | 79.299 | 79.299 | 79.299 | 79.299 | 79.299 |
| (B) | Sodium carboxymethyl cellulose*[1] | 3.5 | 2.5 | 3.5 | 3.5 | 3.5 | 3.5 | 3.5 | 3.5 | 2 | 5 | 7 | 2.2 | 6 |
| (C) | Dried aluminum hydroxide gel | 0.15 | 0.15 | 0.15 | 0.15 | 0.15 | 0.15 | 0.15 | 0.15 | 0.15 | 0.15 | 0.15 | 0.15 | 0.15 |
| (D) | Polyvinyl alcohol*[2] | 5 | 2.7 | 5 | 5 | 5 | 5 | 5 | 5 | 5 | 5 | 5 | 5 | 5 |
| Others | Propylene glycol | 5 | 4 | 5 | 5 | 5 | 5 | 5 | 5 | 5 | 5 | 5 | 5 | 5 |
| | Polyethylene glycol | 0.9 | — | 0.9 | 0.9 | 0.9 | 0.9 | 0.9 | 0.9 | 0.9 | 0.9 | 0.9 | 0.9 | 0.9 |
| | Glycerin | 5 | — | — | 9.3 | 14.3 | 19.3 | 24.3 | 29.3 | 6.5 | 3.5 | 1.5 | 6.3 | 2.5 |
| | Sodium hyaluronate | 0.001 | — | 0.001 | 0.001 | 0.001 | 0.001 | 0.001 | 0.001 | 0.001 | 0.001 | 0.001 | 0.001 | 0.001 |
| | Hydroxyethyl cellulose | 0.1 | — | 0.1 | 0.1 | 0.1 | 0.1 | 0.1 | 0.1 | 0.1 | 0.1 | 0.1 | 0.1 | 0.1 |
| | Menthyl lactate | 0.1 | — | 0.1 | 0.1 | 0.1 | 0.1 | 0.1 | 0.1 | 0.1 | 0.1 | 0.1 | 0.1 | 0.1 |
| | Sodium para-oxybenzoate | 0.25 | 0.25 | 0.25 | 0.25 | 0.25 | 0.25 | 0.25 | 0.25 | 0.25 | 0.25 | 0.25 | 0.25 | 0.25 |
| | Perfume | 0.3 | — | 0.3 | 0.3 | 0.3 | 0.3 | 0.3 | 0.3 | 0.3 | 0.3 | 0.3 | 0.3 | 0.3 |
| | Tartaric acid | — | — | — | — | — | — | — | — | — | — | — | — | — |
| | Succinic acid | 0.4 | 0.4 | 0.4 | 0.4 | 0.4 | 0.4 | 0.4 | 0.4 | 0.4 | 0.4 | 0.4 | 0.4 | 0.4 |
| Total | | 100 | 100 | 100 | 100 | 100 | 100 | 100 | 100 | 100 | 100 | 100 | 100 | 100 |
| Content of sodium carboxymethyl cellulose | | 100 | 100 | 100 | 100 | 100 | 100 | 100 | 100 | 100 | 100 | 100 | 100 | 100 |

TABLE 1-continued

| Components blended | Example 1 | Example 2 | Example 3 | Example 4 | Example 5 | Example 6 | Example 7 | Example 8 | Example 9 | Example 10 | Example 11 | Example 12 | Example 13 |
|---|---|---|---|---|---|---|---|---|---|---|---|---|---|
| in component (B) | | | | | | | | | | | | | |
| (B)/(D) | 0.7 | 0.9 | 0.7 | 0.7 | 0.7 | 0.7 | 0.7 | 0.7 | 0.4 | 1.0 | 1.4 | 0.4 | 1.2 |
| (B)/(C) | 23.3 | 16.7 | 23.3 | 23.3 | 23.3 | 23.3 | 23.3 | 23.3 | 13.3 | 33.3 | 46.7 | 14.7 | 40.0 |
| Feeling of use | 5 | 5 | 5 | 5 | 4 | 4 | 3 | 3 | 5 | 5 | 3 | 5 | 4 |
| Adhesion (sec) | 27 | 13 | 28 | 34 | 11 | 70 | 14.7 | 168 | 13 | 45 | 1 | 19 | 2 |
| Followability | 5 | 5 | 5 | 5 | 5 | 5 | 5 | 5 | 5 | 4 | 3 | 5 | 4 |
| Gel stability | 5 | 3 | 5 | 5 | 5 | 5 | 5 | 5 | 5 | 3 | 4 | 5 | 4 | 5 |

*[1] Etherification degree = 0.7 and viscosity at 25° C. of 1 mass % aqueous solution = 2,750 mPa·s
*[2] GOHSENOL EG-40 (manufactured by the Nippon Synthetic Chemical Industry Co., Ltd.)

TABLE 2

| | Components blended | Example 14 | Example 15 | Example 16 | Example 17 | Example 18 | Example 19 | Example 20 | Example 21 | Comparative Example 1 | Comparative Example 2 | Comparative Example 3 |
|---|---|---|---|---|---|---|---|---|---|---|---|---|
| (A) | Purified water | 79.299 | 79.299 | 79.299 | 79.299 | 79.299 | 79.299 | 79.299 | 79.299 | 44.999 | 79.299 | 79.299 |
| (B) | Sodium carboxymethyl cellulose*[1] | 3.5 | 3.5 | 3.5 | 3.5 | 3.5 | 3.5 | 3.5 | 3.5 | 3.5 | 3.5 | 3.5 |
| (C) | Dried aluminum hydroxide gel | 0.15 | 0.15 | 0.15 | 0.15 | 0.15 | 0.15 | 0.15 | 0.15 | 0.15 | 0.15 | 0.15 |
| (D) | Polyvinyl alcohol[2] | 4 | 7 | 2.5 | 3 | 6 | 8 | — | — | 5 | 2 | 9 |
| | Polyvinyl-pyrrolidone | — | — | — | — | — | — | 5 | — | — | — | — |
| | Polyacrylamide | — | — | — | — | — | — | — | 5 | — | — | — |
| Others | Propylene glycol | 5 | 5 | 5 | 5 | 5 | 5 | 5 | 5 | 5 | 5 | 5 |
| | Polyethylene glycol | 0.9 | 0.9 | 0.9 | 0.9 | 0.9 | 0.9 | 0.9 | 0.9 | 0.9 | 0.9 | 0.9 |
| | Glycerin | 6 | 3 | 7.5 | 7 | 4 | 2 | 5 | 5 | 39.3 | 8 | 1 |
| | Sodium hyaluronate | 0.001 | 0.001 | 0.001 | 0.001 | 0.001 | 0.001 | 0.001 | 0.001 | 0.001 | 0.001 | 0.001 |
| | Hydroxyethyl cellulose | 0.1 | 0.1 | 0.1 | 0.1 | 0.1 | 0.1 | 0.1 | 0.1 | 0.1 | 0.1 | 0.1 |
| | Menthyl lactate | 0.1 | 0.1 | 0.1 | 0.1 | 0.1 | 0.1 | 0.1 | 0.1 | 0.1 | 0.1 | 0.1 |
| | Sodium para-oxybenzoate | 0.25 | 0.25 | 0.25 | 0.25 | 0.25 | 0.25 | 0.25 | 0.25 | 0.25 | 0.25 | 0.25 |
| | Perfume | 0.3 | 0.3 | 0.3 | 0.3 | 0.3 | 0.3 | 0.3 | 0.3 | 0.3 | 0.3 | 0.3 |
| | Tartaric acid | — | — | — | — | — | — | — | — | — | — | — |
| | Succinic acid | 0.4 | 0.4 | 0.4 | 0.4 | 0.4 | 0.4 | 0.4 | 0.4 | 0.4 | 0.4 | 0.4 |
| Total | | 100 | 100 | 100 | 100 | 100 | 100 | 100 | 100 | 100 | 100 | 100 |
| Content of sodium carboxymethyl cellulose in component (B) | | 100 | 100 | 100 | 100 | 100 | 100 | 100 | 100 | 100 | 100 | 100 |
| (B)/(D) | | 0.9 | 0.5 | 1.4 | 1.2 | 0.6 | 0.4 | 0.7 | 0.7 | 0.7 | 1.8 | 0.4 |
| (B)/(C) | | 23.3 | 23.3 | 23.3 | 23.3 | 23.3 | 23.3 | 23.3 | 23.3 | 23.3 | 23.3 | 23.3 |
| Feeling of use | | 5 | 5 | 5 | 5 | 5 | 3 | 5 | 5 | 1 | 5 | 4 |
| Adhesion (sec) | | 16 | 52 | 14 | 13 | 34 | 98 | 1 | 1 | >200 | 12 | 83 |
| Followability | | 5 | 4 | 5 | 5 | 4 | 3 | 5 | 5 | 5 | 5 | 2 |
| Gel stability | | 5 | 4 | 4 | 4 | 5 | 5 | 5 | 5 | 5 | 1 | 5 |

*[1] Etherification degree = 0.7 and viscosity at 25° C. of 1 mass % aqueous solution = 2,750 mPa·s
*[2] GOHSENOL EG-40 (manufactured by the Nippon Synthetic Chemical Industry Co., Ltd.)

TABLE 3

| | Components blended | Example 22 | Example 23 | Comparative Example 4 | Comparative Example 5 | Comparative Example 6 | Comparative Example 7 |
|---|---|---|---|---|---|---|---|
| (A) | Purified water | 79.299 | 79.299 | 79.299 | 44.999 | 44.999 | 44.999 |
| (B) | Sodium carboxymethyl cellulose*[1] | 3.5 | 3.5 | 3.5 | 3.5 | 3.5 | 7 |

TABLE 3-continued

| Components blended | | Example 22 | Example 23 | Comparative Example 4 | Comparative Example 5 | Comparative Example 6 | Comparative Example 7 |
|---|---|---|---|---|---|---|---|
| | Sodium polyacrylate | — | 0.5 | 1.5 | 1.5 | 1.5 | 3 |
| (C) | Dried aluminum hydroxide gel | 1 | 1 | 1 | 1 | 1 | 0.15 |
| (D) | Polyvinyl alcohol*[2] | 5 | 5 | 5 | 5 | 2 | 2 |
| Others | Propylene glycol | 5 | 5 | 5 | 5 | 5 | 5 |
| | Polyethylene glycol | 0.9 | 0.9 | 0.9 | 0.9 | 0.9 | 0.9 |
| | Glycerin | 3.95 | 3.45 | 2.45 | 36.749 | 39.749 | 35.6 |
| | Sodium hyaluronate | 0.001 | 0.001 | 0.001 | 0.001 | 0.001 | 0.001 |
| | Hydroxyethyl cellulose | 0.1 | 0.1 | 0.1 | 0.1 | 0.1 | 0.1 |
| | Menthyl lactate | 0.1 | 0.1 | 0.1 | 0.1 | 0.1 | 0.1 |
| | Sodium para-oxybenzoate | 0.25 | 0.25 | 0.25 | 0.25 | 0.25 | 0.25 |
| | Perfume | 0.3 | 0.3 | 0.3 | 0.3 | 0.3 | 0.3 |
| | Tartaric acid | 0.2 | 0.2 | 0.2 | 0.2 | 0.2 | 0.2 |
| | Succinic acid | 0.4 | 0.4 | 0.4 | 0.4 | 0.4 | 0.4 |
| Total | | 100 | 100 | 100 | 99.999 | 99.999 | 100 |
| Content of sodium carboxymethyl cellulose in component (B) | | 100 | 87.5 | 70 | 70 | 70 | 70 |
| (B)/(D) | | 0.7 | 0.7 | 0.7 | 0.7 | 1.75 | 3.5 |
| (B)/(C) | | 3.5 | 4.0 | 5.0 | 5.0 | 5.0 | 66.7 |
| Feeling of use | | 5 | 4 | 1 | 1 | 1 | 1 |
| Adhesion (sec) | | 1 | 25 | >200 | >200 | >200 | >200 |
| Followability | | 5 | 4 | 4 | 3 | 3 | * |
| Gel stability | | 3 | 3 | 3 | 3 | 4 | 1 |

*[1]Etherification degree = 0.7 and viscosity at 25° C. of 1 mass % aqueous solution = 2,750 mPa · s
*[2]GOHSENOL EG-40 (manufactured by the Nippon Synthetic Chemical Industry Co., Ltd.)
* Unevaluable (Insufficient shape retention)

TABLE 4

| Non-woven fabric used | Example 1 | Comparative Example 4 | Comparative Example 5 | Comparative Example 6 |
|---|---|---|---|---|
| Non-woven fabric 1 | 5 | 2 | 3 | 4 |
| Non-woven fabric 2 | 5 | 1 | 1 | 1 |

The results of Tables 1 to 3 revealed that, as compared with Comparative Examples 1 to 6 with a content of component (A) or component (D), or a content of carboxymethylcellulose or a salt thereof in component (B) being out of the aforementioned ranges, Examples 1 to 23 have excellent followability to the skin and high gel stability while giving good feeling of use.

Further, the results of Table 4 revealed that the hydrogel composition of the present invention does not bleed over a long period of time, even when it is layered on a water absorbent fibers, and thus can be combined with a wide range of materials.

The invention claimed is:
1. A hydrogel composition, comprising components (A) to (D) below:
(A) water in an amount of 60 mass % to 95 mass %, based on a mass of the hydrogel composition;
(B) one or more anionic water-soluble polymer compounds, in a total amount of 2 mass % to 7 mass %, based on the mass of the hydrogel composition, wherein said one or more anionic water-soluble polymer compounds comprise 80 mass % or more of carboxymethylcellulose or a salt thereof;
(C) a crosslinking agent that forms ionic crosslinking with an anionic functional group; and
(D) a nonionic water-soluble polymer compound, in an amount of 2.5 mass % to 8 mass %, based on the mass of the hydrogel composition, represented by formula (1) below:

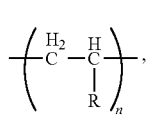

(1)

where R denotes —OH, —NX$_2$, —OCH$_3$, —NHCOCH$_3$, —NCH$_3$COCH$_3$, —CONH$_2$, or

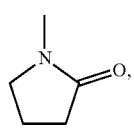

X if present denotes —CH$_3$ or a hydrogen atom, and n is a numerical value from 200 to 500,000;
wherein a mass ratio of component (B) to component (D), ((B)/(D)), is in a range of 0.4 to 1.2.
2. The hydrogel composition according to claim 1, wherein the component (C) is one or more selected from the group consisting of a polyvalent metal compound and a cationic compound having at least two monovalent cation elements and/or amino groups in one molecule.

3. The hydrogel composition according to claim 1, wherein a content of at least one water-soluble polymer compound other than the component (B) and the component (D), if the at least one water-soluble polymer compound is present, is 1 mass % or less.

4. The hydrogel composition according to claim 1, wherein a mass ratio of the component (B) to the component (C), ((B)/(C)), is 3 to 60.

5. The hydrogel composition according to claim 1, wherein the component (D) is one or more selected from the group consisting of polyvinyl alcohol, polyvinylpyrrolidone, and polyacrylamide.

6. The hydrogel composition according to claim 1, wherein the total amount of the component (B) is 2.2 mass % to 6 mass %, based on the mass of the hydrogel composition.

7. The hydrogel composition according to claim 1, wherein the hydrogel composition has a thickness of 0.1 mm or more and 4 mm or less.

8. A method for producing a hydrogel composition, comprising:
mixing components (A) to (D) below to prepare an uncrosslinked gel stock solution:
(A) water in an amount of 60 mass % to 95 mass %, based on a mass of the uncrosslinked gel stock solution;
(B) one or more anionic water-soluble polymer compounds, in a total amount of 2 mass % to 7 mass %, based on the mass of the uncrosslinked gel stock solution, wherein said one or more anionic water-soluble polymer compounds comprise 80 mass % or more of carboxymethylcellulose or a salt thereof;
(C) a crosslinking agent that forms ionic crosslinking with an anionic functional group; and
(D) a nonionic water-soluble polymer compound, in an amount of 2.5 mass % to 8 mass %, based on the mass of the uncrosslinked gel stock solution, represented by formula (1) below:

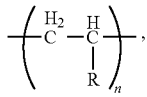

where R denotes —OH, —NX$_2$, —OCH$_3$, —NHCOCH$_3$, —NCH$_3$COCH$_3$, —CONH$_2$, or

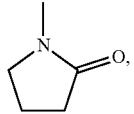

X if present denotes —CH$_3$ or a hydrogen atom, and n is a numerical value from 200 to 500,000;
wherein a mass ratio of component (B) to component (D), ((B)/(D)), is in a range of 0.4 to 1.2; and
subsequently sandwiching the uncrosslinked gel stock solution between a first peelable film and a second peelable film or a base material layer thereby making the uncrosslinked gel stock solution into a sheet.

9. The hydrogel composition according to claim 1, wherein an etherification degree of the carboxymethylcellulose or the salt thereof in the component (B) is from 0.65 to 0.9.

10. The hydrogel composition according to claim 1, wherein said one or more anionic water-soluble polymer compounds (B) comprise 90 mass % or more of the carboxymethylcellulose or the salt thereof.

11. The hydrogel composition according to claim 1, wherein a mass ratio of the component (B) to the component (C), ((B)/(C)), is 15 or more and 40 or less.

12. The hydrogel composition according to claim 1, wherein the component (A) is present in an amount of 70 mass % to 90 mass %, based on the mass of the hydrogel composition.

13. The hydrogel composition according claim 1, wherein the hydrogel composition is layered on a base material.

14. An adhesive sheet for cooling, comprising:
the hydrogel composition according to claim 1, wherein the hydrogel composition is layered on a base material.

15. The hydrogel composition according to claim 1, wherein the component (D) is one or more nonionic water-soluble polymer compounds selected from the group consisting of polyvinyl alcohol, polyvinylpyrrolidone, polyacrylamide, and polyvinylmethylether, in a total amount of 2.5 mass % to 8 mass %, based on the mass of the hydrogel composition.

16. The method according to claim 8, wherein the component (D) is one or more nonionic water-soluble polymer compounds selected from the group consisting of polyvinyl alcohol, polyvinylpyrrolidone, polyacrylamide, and polyvinylmethylether, in a total amount of 2.5 mass % to 8 mass %, based on the mass of the uncrosslinked gel stock solution.

17. The hydrogel composition according to claim 1, wherein the component (D) is one or more nonionic water-soluble polymer compounds selected from the group consisting of polyvinyl alcohol, polyvinylpyrrolidone, and polyacrylamide, in a total amount of 2.5 mass % to 8 mass %, based on the mass of the hydrogel composition.

18. The method according to claim 8, wherein the component (D) is one or more nonionic water-soluble polymer compounds selected from the group consisting of polyvinyl alcohol, polyvinylpyrrolidone, and polyacrylamide, in a total amount of 2.5 mass % to 8 mass %, based on the mass of the uncrosslinked gel stock solution.

* * * * *